US011058858B2

(12) United States Patent
Avula et al.

(10) Patent No.: US 11,058,858 B2
(45) Date of Patent: Jul. 13, 2021

(54) DISINFECTING CAP FOR VALVED CONNECTORS AND METHOD OF USE

(71) Applicant: Merit Medical Systems, Inc., South Jordan, UT (US)

(72) Inventors: Mahender Avula, Sandy, UT (US); Kenneth Sykes, Bluffdale, UT (US); Richard P. Jenkins, Bluffdale, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 119 days.

(21) Appl. No.: 16/150,966

(22) Filed: Oct. 3, 2018

(65) Prior Publication Data

US 2019/0099593 A1 Apr. 4, 2019

Related U.S. Application Data

(60) Provisional application No. 62/568,037, filed on Oct. 4, 2017.

(51) Int. Cl.
*A61M 39/00* (2006.01)
*A61M 39/16* (2006.01)
*A61M 39/20* (2006.01)
*A61M 39/18* (2006.01)

(52) U.S. Cl.
CPC ........ *A61M 39/165* (2013.01); *A61M 39/162* (2013.01); *A61M 39/18* (2013.01); *A61M 39/20* (2013.01)

(58) Field of Classification Search
CPC .. A61M 39/165; A61M 39/162; A61M 39/18; A61M 39/20; A61M 39/16; A61M 25/0097; Y10S 604/905; B65D 41/02
See application file for complete search history.

(56) References Cited

U.S. PATENT DOCUMENTS

| 1,744,026 | A | 10/1926 | Baltzley |
| 1,868,200 | A | 7/1932 | Freedman |
| 2,356,969 | A | 5/1942 | Blum |
| 2,299,037 | A | 10/1942 | Saueressig |
| 2,351,804 | A | 6/1944 | Blum |
| 3,315,830 | A | 4/1967 | Flynn |

(Continued)

FOREIGN PATENT DOCUMENTS

| CN | 205549223 | 9/2016 |
| EP | 0229786 | 7/1987 |

(Continued)

OTHER PUBLICATIONS

Maki, et al., In Vitro Studies of a Novel Antimicrobial Luer-Activated Needleless Connector for Prevention of Catheter-Related Blookstream Infection, Clinical Infection Diseases, vol. 50, Issue 12 ,Jun. 15, 2010 ,1580-1587.

(Continued)

*Primary Examiner* — William R Carpenter
(74) *Attorney, Agent, or Firm* — Stoel Rives LLP

(57) ABSTRACT

Devices used to disinfect and maintain sterility of a medical valve connector are disclosed. The devices may comprise an insert that is configured to dispense disinfecting solution when the device is coupled to the medical valve connector. Insert grooves are configured to collapse sequentially as the insert is compressed by the medical valve connector.

18 Claims, 10 Drawing Sheets

(56) References Cited

U.S. PATENT DOCUMENTS

| | | | |
|---|---|---|---|
| 3,431,548 A | 3/1969 | Busler | |
| 3,446,596 A | 5/1969 | Salivar et al. | |
| 3,976,311 A | 8/1976 | Spendlove | |
| 3,987,930 A | 10/1976 | Fuson | |
| 4,121,727 A | 10/1978 | Robbins et al. | |
| 4,232,677 A | 11/1980 | Leibinsohn | |
| 4,299,330 A | 11/1981 | Walter | |
| 4,324,239 A | 4/1982 | Gordon et al. | |
| 4,334,551 A | 6/1982 | Pfister | |
| 4,344,551 A | 6/1982 | Pfister | |
| 4,340,052 A | 7/1982 | Dennehey et al. | |
| 4,346,703 A | 8/1982 | Dennehey et al. | |
| 4,354,490 A | 10/1982 | Rogers | |
| 4,369,781 A | 1/1983 | Gilson et al. | |
| 4,402,691 A | 9/1983 | Rosenthal et al. | |
| 4,432,764 A * | 2/1984 | Lopez | A61M 39/162 |
| | | | 604/533 |
| 4,432,766 A | 2/1984 | Bellotti et al. | |
| 4,440,207 A | 4/1984 | Genatempo et al. | |
| 4,450,624 A | 5/1984 | Collier | |
| 4,572,373 A | 2/1986 | Johansson | |
| 4,597,758 A | 7/1986 | Aalto et al. | |
| 4,624,664 A | 11/1986 | Peluso et al. | |
| 4,667,837 A | 5/1987 | Vitello et al. | |
| 4,671,306 A | 6/1987 | Spector | |
| 4,778,447 A | 10/1988 | Velde et al. | |
| 4,798,303 A | 1/1989 | Arnold | |
| 4,810,241 A | 3/1989 | Rogers | |
| 4,838,875 A | 6/1989 | Somor | |
| D303,631 S | 9/1989 | Demarest | |
| D310,542 S | 9/1990 | Regnault | |
| 4,991,629 A | 2/1991 | Ernesto et al. | |
| 5,006,114 A | 4/1991 | Rogers et al. | |
| 5,184,742 A | 2/1993 | Decaprio et al. | |
| D333,788 S | 3/1993 | Geschwender | |
| 5,190,534 A | 3/1993 | Kendell | |
| 5,195,957 A | 3/1993 | Tollini | |
| 5,205,821 A | 4/1993 | Kruger et al. | |
| 5,242,425 A | 9/1993 | White et al. | |
| D340,112 S | 10/1993 | Zeman | |
| D341,227 S | 11/1993 | Lang et al. | |
| 5,269,771 A | 12/1993 | Thomas et al. | |
| 5,385,372 A | 1/1995 | Utterberg | |
| 5,439,451 A | 8/1995 | Collinson et al. | |
| 5,445,270 A | 8/1995 | Dratz | |
| 5,451,113 A | 9/1995 | Lund et al. | |
| 5,466,219 A | 11/1995 | Lynn et al. | |
| 5,492,147 A | 2/1996 | Challender et al. | |
| 5,536,258 A | 7/1996 | Folden | |
| 5,554,135 A | 9/1996 | Menyhay | |
| 5,620,427 A | 4/1997 | Werschmidt et al. | |
| 5,624,057 A | 4/1997 | Lifshey | |
| 5,694,978 A | 12/1997 | Heilmann et al. | |
| 5,702,017 A | 12/1997 | Goncalves | |
| 5,738,663 A | 4/1998 | Lopez | |
| 5,792,120 A | 8/1998 | Menyhay | |
| 5,839,715 A * | 11/1998 | Leinsing | A61J 1/2096 |
| | | | 251/149.1 |
| 5,894,015 A | 4/1999 | Rechtin | |
| 5,951,519 A | 9/1999 | Utterberg | |
| 5,954,657 A | 9/1999 | Rados | |
| 5,954,957 A | 9/1999 | Chin-Loy et al. | |
| 6,045,539 A | 4/2000 | Menyhay | |
| 6,152,913 A | 11/2000 | Feith et al. | |
| 6,171,287 B1 | 1/2001 | Lynn et al. | |
| D456,668 S | 5/2002 | Tse | |
| D468,015 S | 12/2002 | Horppu | |
| D470,888 S | 2/2003 | Kuboshima | |
| 6,523,686 B1 | 2/2003 | Bae | |
| 6,932,795 B2 | 8/2005 | Lopez et al. | |
| 6,960,191 B2 | 11/2005 | Howlett et al. | |
| 7,014,169 B2 | 3/2006 | Newton et al. | |
| 7,040,598 B2 | 5/2006 | Raybuck | |
| 7,040,669 B2 | 5/2006 | Kenmotsu et al. | |
| 7,198,611 B2 | 4/2007 | Connell et al. | |
| D545,964 S | 7/2007 | Blanco | |
| D547,446 S | 7/2007 | Racz et al. | |
| D550,355 S | 9/2007 | Racz et al. | |
| 7,282,186 B2 | 10/2007 | Lake, Jr. et al. | |
| 7,316,669 B2 | 1/2008 | Ranalletta | |
| D573,643 S | 7/2008 | Brigham et al. | |
| D607,325 S | 1/2010 | Rogers et al. | |
| 7,762,524 B2 | 7/2010 | Cawthon et al. | |
| 7,762,988 B1 | 7/2010 | Vitello | |
| 7,763,006 B2 | 7/2010 | Tennican | |
| 7,780,794 B2 | 8/2010 | Rogers et al. | |
| D632,574 S | 2/2011 | Huntington et al. | |
| 7,922,701 B2 | 4/2011 | Buchman | |
| D639,421 S | 6/2011 | Sano et al. | |
| 7,985,302 B2 | 7/2011 | Rogers et al. | |
| 8,167,847 B2 | 5/2012 | Anderson et al. | |
| 8,172,825 B2 | 5/2012 | Solomon et al. | |
| 8,177,761 B2 | 5/2012 | Howlett et al. | |
| 8,197,749 B2 | 6/2012 | Howlett et al. | |
| 8,231,587 B2 * | 7/2012 | Solomon | A61M 39/162 |
| | | | 604/265 |
| 8,231,602 B2 | 7/2012 | Anderson et al. | |
| 8,273,303 B2 | 9/2012 | Ferlic et al. | |
| 8,328,767 B2 | 12/2012 | Solomon et al. | |
| 8,343,112 B2 | 1/2013 | Solomon et al. | |
| 8,419,713 B1 | 4/2013 | Solomon et al. | |
| 8,523,830 B2 | 9/2013 | Solomon et al. | |
| 8,523,831 B2 * | 9/2013 | Solomon | A61M 39/162 |
| | | | 604/256 |
| 8,641,681 B2 | 2/2014 | Solomon et al. | |
| 8,647,308 B2 | 2/2014 | Solomon et al. | |
| 8,647,326 B2 | 2/2014 | Solomon et al. | |
| 8,740,864 B2 | 6/2014 | Hoang | |
| 8,784,388 B2 | 7/2014 | Charles et al. | |
| 8,808,637 B2 | 8/2014 | Ferlic | |
| 8,961,475 B2 | 2/2015 | Solomon et al. | |
| 9,079,692 B2 | 7/2015 | Solomon et al. | |
| 9,101,750 B2 | 8/2015 | Solomon et al. | |
| 9,114,915 B2 | 8/2015 | Solomon et al. | |
| 9,242,084 B2 | 1/2016 | Solomon et al. | |
| 9,283,369 B2 * | 3/2016 | Ma | A61M 39/20 |
| 9,352,140 B2 | 5/2016 | Kerr et al. | |
| 2002/0093192 A1 | 7/2002 | Matkovich | |
| 2003/0140441 A1 | 7/2003 | Stafford | |
| 2003/0153865 A1 | 8/2003 | Connell et al. | |
| 2003/0181849 A1 | 9/2003 | Castellanos | |
| 2003/0198502 A1 | 10/2003 | Maloney et al. | |
| 2004/0039341 A1 | 2/2004 | Ranalletta | |
| 2004/0195136 A1 | 10/2004 | Young et al. | |
| 2004/0201216 A1 | 10/2004 | Segal et al. | |
| 2004/0214316 A1 | 10/2004 | O'Connell | |
| 2004/0258560 A1 | 12/2004 | Lake, Jr. et al. | |
| 2005/0033267 A1 | 2/2005 | Decaria | |
| 2005/0038397 A1 | 2/2005 | Newton et al. | |
| 2005/0124970 A1 | 6/2005 | Kunin et al. | |
| 2005/0147524 A1 | 7/2005 | Bousquet | |
| 2005/0183971 A1 | 8/2005 | Petricca | |
| 2005/0203460 A1 | 9/2005 | Kim | |
| 2005/0245883 A1 | 11/2005 | Baldwin | |
| 2005/0265773 A1 | 12/2005 | De Laforcade | |
| 2005/0266714 A1 | 12/2005 | Higgins et al. | |
| 2006/0030827 A1 | 2/2006 | Raulerson et al. | |
| 2007/0112333 A1 | 5/2007 | Hoang et al. | |
| 2007/0202177 A1 | 8/2007 | Hoang | |
| 2007/0282280 A1 | 12/2007 | Tennican | |
| 2007/0287989 A1 | 12/2007 | Crawford et al. | |
| 2007/0293818 A1 | 12/2007 | Stout et al. | |
| 2007/0293822 A1 | 12/2007 | Crawford et al. | |
| 2008/0019889 A1 | 1/2008 | Rogers et al. | |
| 2008/0021381 A1 | 1/2008 | Lurvey et al. | |
| 2008/0027399 A1 | 1/2008 | Harding et al. | |
| 2008/0033371 A1 | 2/2008 | Updegraff et al. | |
| 2008/0038167 A1 | 2/2008 | Lynn | |
| 2008/0039803 A1 | 2/2008 | Lynn | |
| 2008/0097407 A1 | 2/2008 | Plishka | |
| 2008/0086091 A1 | 4/2008 | Anderson et al. | |
| 2008/0095680 A1 | 4/2008 | Steffens et al. | |
| 2008/0105704 A1 | 5/2008 | Pritchard | |
| 2008/0107564 A1 | 5/2008 | Sternberg et al. | |

(56) References Cited

U.S. PATENT DOCUMENTS

| | | | |
|---|---|---|---|
| 2008/0132880 A1* | 6/2008 | Buchman | A61M 39/162 604/533 |
| 2008/0147047 A1 | 6/2008 | Davis et al. | |
| 2008/0177250 A1 | 7/2008 | Howlett et al. | |
| 2008/0190485 A1 | 8/2008 | Guala | |
| 2008/0235888 A1 | 10/2008 | Vaillancourt et al. | |
| 2009/0008393 A1* | 1/2009 | Howlett | A61M 39/162 220/380 |
| 2009/0062766 A1 | 3/2009 | Howlett et al. | |
| 2009/0099529 A1 | 4/2009 | Anderson et al. | |
| 2009/0149819 A1* | 6/2009 | Chelak | A61M 39/10 604/246 |
| 2009/0205151 A1 | 8/2009 | Fisher et al. | |
| 2010/0003067 A1 | 1/2010 | Shaw et al. | |
| 2010/0047123 A1 | 2/2010 | Solomon et al. | |
| 2010/0049170 A1 | 2/2010 | Solomon et al. | |
| 2010/0063482 A1 | 3/2010 | Mansour et al. | |
| 2010/0100056 A1 | 4/2010 | Cawthon et al. | |
| 2010/0242993 A1 | 9/2010 | Hoang et al. | |
| 2010/0306938 A1 | 12/2010 | Rogers et al. | |
| 2010/0313366 A1 | 12/2010 | Rogers et al. | |
| 2011/0044850 A1 | 2/2011 | Solomon et al. | |
| 2011/0054440 A1 | 3/2011 | Lewis | |
| 2011/0064512 A1 | 3/2011 | Shaw et al. | |
| 2011/0064515 A1 | 3/2011 | Ruckey et al. | |
| 2011/0165020 A1 | 7/2011 | Truggvason | |
| 2011/0213341 A1* | 9/2011 | Solomon | A61M 39/162 604/533 |
| 2011/0217212 A1 | 9/2011 | Solomon et al. | |
| 2011/0232020 A1 | 9/2011 | Rogers et al. | |
| 2011/0277788 A1 | 11/2011 | Rogers et al. | |
| 2011/0314619 A1 | 12/2011 | Schweikert | |
| 2012/0016318 A1 | 1/2012 | Hoang et al. | |
| 2012/0039764 A1 | 2/2012 | Solomon | |
| 2012/0039765 A1 | 2/2012 | Solomon | |
| 2012/0082977 A1 | 4/2012 | Rajagopal et al. | |
| 2012/0216359 A1 | 8/2012 | Rogers et al. | |
| 2013/0019421 A1 | 1/2013 | Rogers et al. | |
| 2013/0072908 A1 | 3/2013 | Solomon et al. | |
| 2013/0171030 A1 | 7/2013 | Ferlic et al. | |
| 2013/0197485 A1 | 8/2013 | Gardner et al. | |
| 2014/0010481 A1 | 1/2014 | Last et al. | |
| 2014/0135739 A1 | 5/2014 | Solomon et al. | |
| 2014/0227144 A1 | 8/2014 | Liu et al. | |
| 2015/0231384 A1 | 8/2015 | Ma et al. | |
| 2015/0273199 A1 | 10/2015 | Adams et al. | |
| 2015/0374968 A1 | 12/2015 | Solomon et al. | |
| 2016/0038701 A1 | 2/2016 | White et al. | |
| 2016/0045629 A1 | 2/2016 | Gardner et al. | |
| 2016/0106968 A1 | 4/2016 | Solomon et al. | |
| 2017/0245618 A1 | 8/2017 | Chen et al. | |
| 2019/0209781 A1 | 7/2019 | Solomon et al. | |

FOREIGN PATENT DOCUMENTS

| | | |
|---|---|---|
| EP | 0462355 | 12/1991 |
| JP | 64002760 | 1/1989 |
| WO | 2004035245 | 4/2004 |
| WO | 2006099306 A2 | 9/2006 |
| WO | 2007097985 | 10/2007 |
| WO | 2008089196 A2 | 7/2008 |
| WO | 2008100950 A2 | 8/2008 |
| WO | 2010002808 A1 | 1/2010 |
| WO | 2010141508 A1 | 12/2010 |
| WO | 2011141508 | 12/2010 |
| WO | 2011053924 A1 | 5/2011 |
| WO | 2011066565 A1 | 6/2011 |
| WO | 2011066586 A1 | 6/2011 |
| WO | 2013184716 | 12/2013 |
| WO | 2015174953 | 11/2015 |

OTHER PUBLICATIONS

Menyhay, et al., Disinfection of Needleless Catheter Connecors and Access Ports with Alcohol May Not Prevent Microbial Entry: The Promise of a Novel Antiseptic-Barrier Cap, Infection control and Hospital Epidemiology, vol. 27 No. 1 ,Jan. 2006 ,23-27.
International Search Report and Written Opinion dated Jan. 24, 2019 for PCT/US2018/054202.
Office Action dated Mar. 27, 2019 for U.S. Appl. No. 14/797,533.
European Search Report dated Jun. 13, 2019 for EP16866954.7.
Office Action dated Jun. 3, 2019 for U.S. Appl. No. 14/978,925.
Office Action dated Jul. 17, 2019 for U.S. Appl. No. 14/797,533.
European Search Report dated Jun. 9, 2020 for EP18744486.4.
Office Action dated Jun. 25, 2020 for U.S. Appl. No. 16/235,584.
Notice of Allowance dated Dec. 19, 2019 for U.S. Appl. No. 15/979,213.
Office Action dated Jul. 23, 2020 for U.S. Appl. No. 14/797,533.
European Search Report dated Mar. 6, 2012 for EP08727689.5.
European Search Report dated Jun. 20, 2017 for EP10827614.8.
International Search Report and the Written Opinion dated Jan. 26, 2011 for PCT/US2010/058404.
International Search Report and Written Opinion dated Jan. 6, 2011 for PCT/US2010/054995.
International Search Report and Written Opinion dated Feb. 1, 2017 for PCT/US2016/062061.
International Search Report and Written Opinion dated Feb. 7, 2011 for PCT/US2010/058453.
International Search Report and Written Opinion dated Jun. 22, 2018 for PCT/US2018/014237.
International Search Report with Written Opinion dated Aug. 31, 2009 for PCT/US2009/049094.
Notice of Allowance dated Jun. 7, 2017 for U.S. Appl. No. 14/162,207.
Notice of Allowance dated Sep. 1, 2017 for U.S. Appl. No. 14/162,207.
Notice of Allowance dated Sep. 17, 2018 for U.S. Appl. No. 14/845,004.
Notice of Allowance dated Oct. 25, 2018 for U.S. Appl. No. 14/947,341.
Notice of Allowance dated Nov. 9, 2018 for U.S. Appl. No. 15/203,002.
Office Action dated Jan. 27, 2010 for U.S. Appl. No. 12/014,388.
Office Action dated Feb. 27, 2018 for U.S. Appl. No. 14/978,925.
Office Action dated Apr. 4, 2018 for U.S. Appl. No. 14/845,004.
Office Action dated Apr. 22, 2011 for U.S. Appl. No. 12/164,310.
Office Action dated Apr. 26, 2018 for U.S. Appl. No. 14/797,533.
Office Action dated May 5, 2009 for U.S. Appl. No. 12/014,388.
Office Action dated May 25, 2018 for U.S. Appl. No. 15/203,002.
Office Action dated Jun. 7, 2018 for U.S. Appl. No. 14/947,341.
Office Action dated Jun. 9, 2011 for U.S. Appl. No. 12/171,997.
Office Action dated Jun. 21, 2010 for U.S. Appl. No. 12/014,388.
Office Action dated Aug. 16, 2010 for U.S. Appl. No. 12/164,310.
Office Action dated Sep. 14, 2018 for U.S. Appl. No. 14/978,925.
Office Action dated Oct. 20, 2017 for U.S. Appl. No. 15/203,002.
Office Action dated Nov. 17, 2017 for U.S. Appl. No. 14/845,004.
Office Action dated Nov. 29, 2018 for U.S. Appl. No. 14/797,533.
Office Action dated Dec. 23, 2010 for U.S. Appl. No. 12/014,388.
Baxa Corporation Launches PadLock Set Saver for IV Safety press release, 2 pages, available at http://www.pr.com/press-release/55432. ,Oct. 10, 2007.
Baxa Corporation Padlock catalog, 3 pages, copyright 2009, available at http://www.baxa.com/SearchResults/ ProductDetail/?id=6452BFB9-3048-7B87-701697FB93902BA6.
Baxa Corporation Padlock Microbial Testing Technical Paper, copyright 2007, 4 pages, available at http://www.baxa.com/resources/docs/technicalPapers/PadLockMicrobialChallengeTechPaper.pdf.
Baxa Corporation PadLock Set Saver Specifications and Instructions for Use, copyright 2007, 2 pages, available at http://www.baxa.com/resources/docs/5300103905C.pdf.
BD Q-Syte Luer Access Split Septum product brochure, 4 pages, available at http://www.bd.com/infusion/pdfs/D16333.pdf. ,Nov. 2008.
Braun product catalog, 2pages. ,Aug. 2008.

(56) References Cited

OTHER PUBLICATIONS

Curos Port Protector, web page from http://www.iveramed.com/ ,Jul. 11, 2008.
Curos Port Protector product brochure, 2 pages, available at http://www.iveramed.com/clocs/Curos%20Brochure-FINAL.pdf. ,Nov. 2008.
Hospira Male/Female Sterile Cap product packaging insert and brochure, 2 pages. ,Aug. 2004.
Kippmed Vented Non-Vented Female Luer Lock Caps, The KippGroup, ,Jan. 1995 ,2 pgs.
Tego Connector product brochure, 2 pages, available at http://www.icumed.com/Docs-Tego/M1-1148%20TEG0%20Folder%20Brochure%20Rev.3.pdf. ,Nov. 2008.
Unomedical Medical Products catalog, 2 pages, available at http://www.unomedical.net/au/section05/section10/ LocalSSI/..%5C..%5Cpdf%5Cmedical.pdf ,Jan. 2006.
Buchman, et al., A New Central Venous Catheter Cap: Decreased Microbial Growth and Risk for Catheter-Related Bloodstream Infection, The Journal of Vascular Access ,2009 ,11-21.
Office Action dated Aug. 30, 2019 for U.S. Appl. No. 15/979,213.
International Search Report and Written Opinion dated Jan. 8, 2008 for PCT/US2008/051087.
Stoker, et al., One Less Problem, Safe Practices when Administering IV Therapy, Managing Infection Control, 4 pgs ,Jun. 2008.
European Search Report dated Mar. 25, 2020 for EP15808498.8.
Office Action dated Mar. 4, 2021 for U.S. Appl. No. 14/797,533.
Office Action dated Mar. 8, 2021 for U.S. Appl. No. 16/235,584.

\* cited by examiner

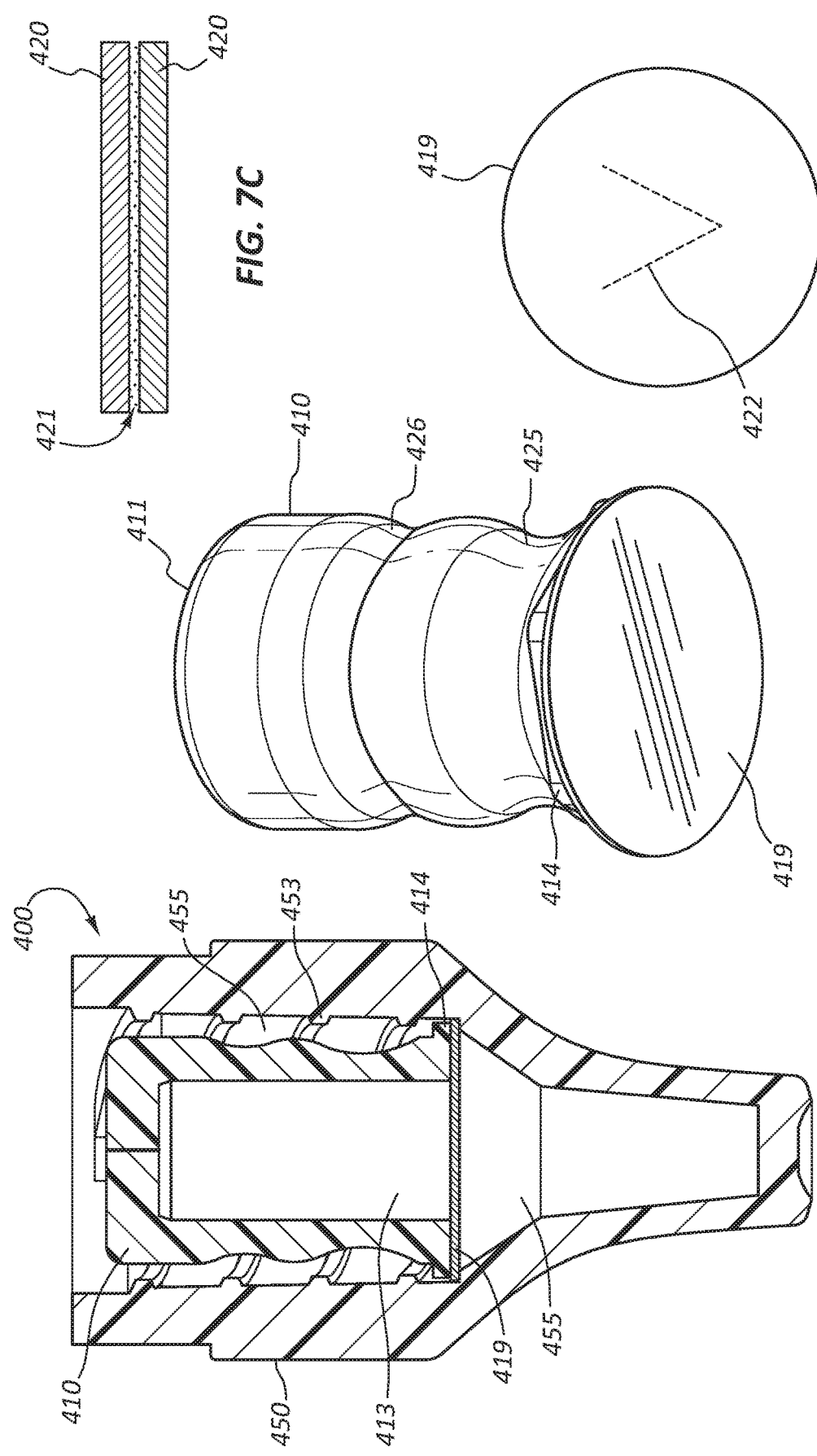

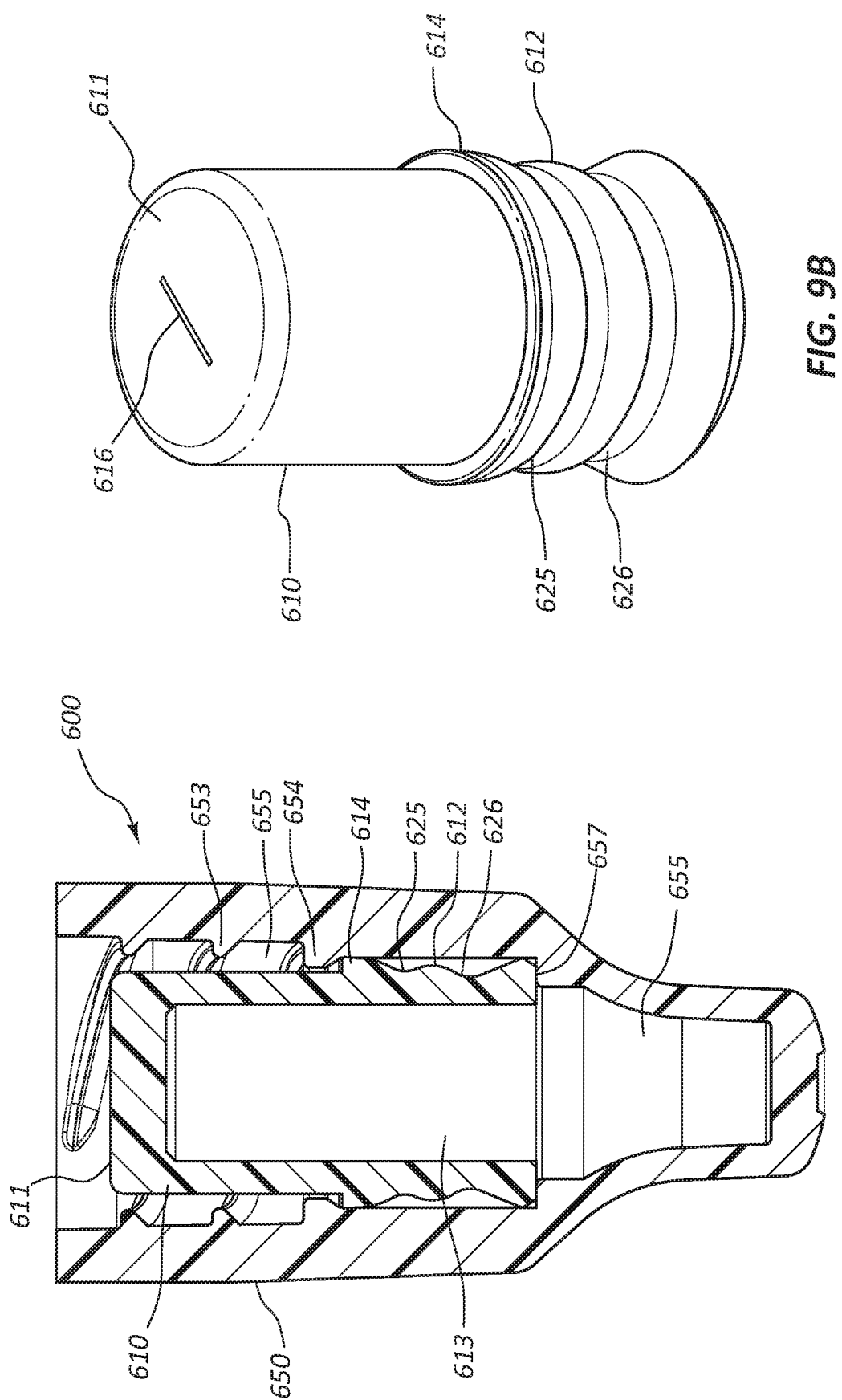

DISINFECTING CAP FOR VALVED CONNECTORS AND METHOD OF USE

RELATED APPLICATIONS

This application claims priority to U.S. Provisional Application No. 62/568,037, filed on Oct. 4, 2017 and titled "Disinfecting Cap For Valved Connectors And Method Of Use" which is hereby incorporated by reference in its entirety.

TECHNICAL FIELD

The present disclosure relates generally to medical devices. More specifically, the present disclosure relates to medical devices and systems for providing infection control for infusion therapy and access devices.

BRIEF DESCRIPTION OF THE DRAWINGS

The embodiments disclosed herein will become more fully apparent from the following description and appended claims, taken in conjunction with the accompanying drawings. The drawings are not necessarily drawn to scale unless specifically indicated. The drawings depict only typical embodiments, which embodiments will be described with additional specificity and detail in connection with the drawings in which:

FIG. 7A is a perspective view of an embodiment of the disinfecting cap having a laminate seal.

FIG. 7B is a perspective view of the insert and laminate seal of the disinfecting cap of FIG. 7A.

FIG. 7C is a cross section view of a portion of the laminate seal of the disinfecting cap of FIG. 7A.

FIG. 7D is a top view of the laminate seal of the disinfecting cap of FIG. 7A.

FIG. 9A is a cross section view of an embodiment of the disinfecting cap having an annular retention ring.

FIG. 9B is a perspective view of the insert of the disinfecting cap of FIG. 9A.

DETAILED DESCRIPTION

Figures 1A, 1B:
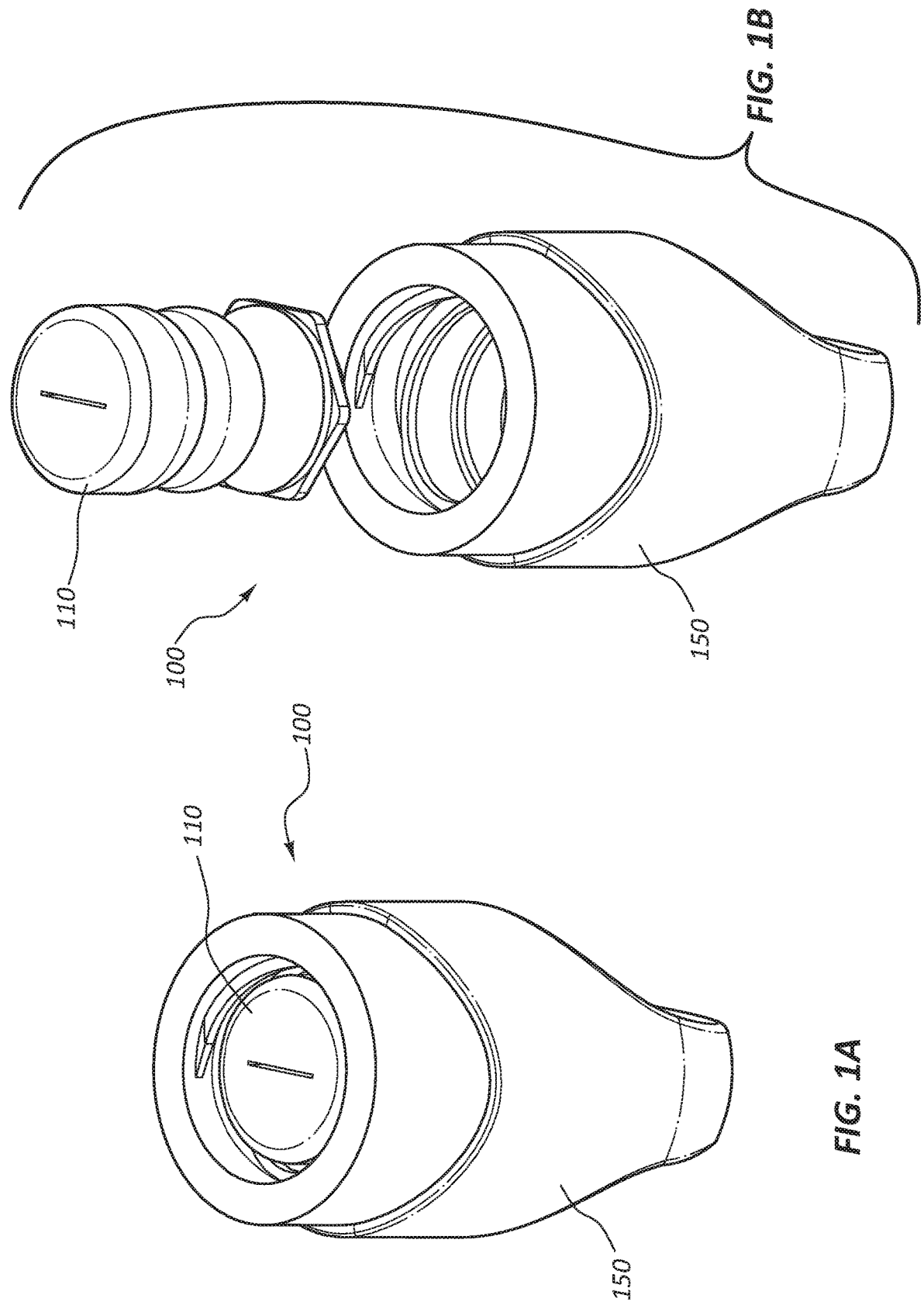
FIG. 1A is a perspective view of a disinfecting cap.
FIG. 1B is an exploded view of the components of the disinfecting cap of FIG. 1A.

Infusion therapy procedures are some of the most common procedures performed in a clinical care environment and the source of nosocomial infections, such as catheter related blood stream infections (CRBSI). CRBSIs may lead to serious morbidities, increased healthcare costs, and death. Many medical devices have been developed to reduce the risk of CRBSI to patients being treated with infusion therapy. These devices include disinfecting caps configured to disinfect and maintain sterility of needleless access devices or valved connectors. In some embodiments, disinfecting caps include a female cap configured to couple with a medical valve connector, a disinfecting solution such as alcohol, and a disinfecting solution reservoir and dispensing feature. Further, certain disinfecting caps are configured to bathe the medical valve connector in the disinfecting solution between uses of the medical valve connector to disinfect the medical valve connector from contamination and prevent infection of the patient. The disinfecting caps may be provided at the patient's bedside for convenience and to support consistent use by a healthcare worker Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from a healthcare worker during use. The proximal end refers to the opposite end, or the end nearest the healthcare worker during use.

FIGS. 1A-9B illustrate different views of disinfecting caps and related components. In certain views each disinfecting cap may be coupled to, or shown with, additional components not included in every view. Further, in some views only selected components are illustrated, to provide detail into the relationship of the components. Some components may be shown in multiple views but not discussed in connection with every view. Disclosure provided in connection with any figure is relevant and applicable to the disclosure provided in connection with any figure or embodiment.

FIGS. 1A-3B depict an embodiment of a disinfecting cap 100. In the illustrated embodiment, the disinfecting cap 100 is comprised of an insert 110 and female cap 150. The insert 110 is disposed and retained within the female cap 150.

Figure 2A:
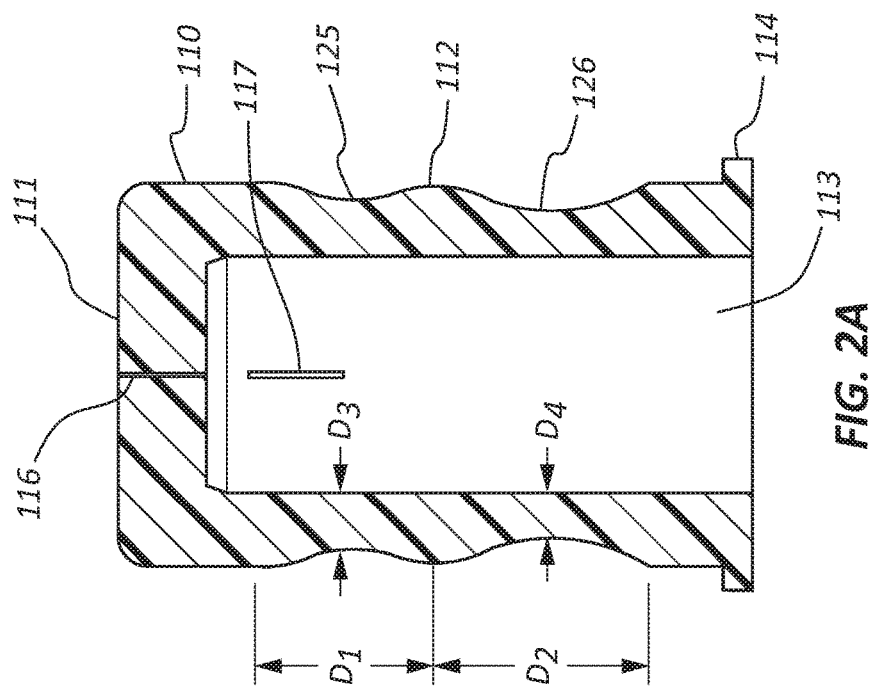
FIG. 2A is a longitudinal cross section view of an insert of the disinfecting cap of FIG. 1A.
Figure 2B:
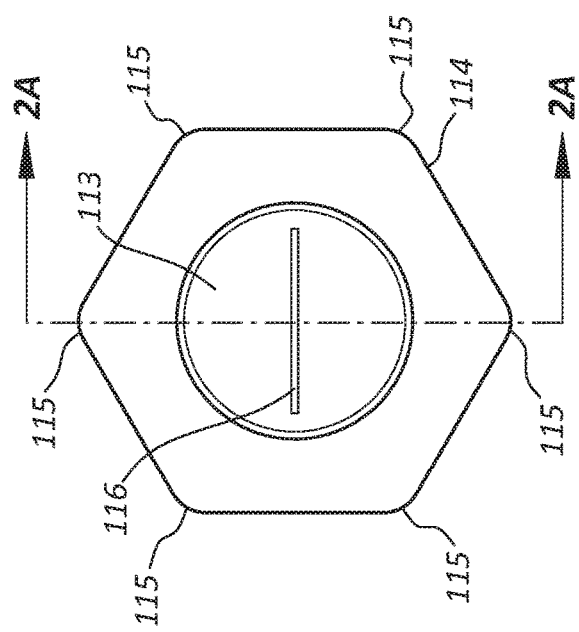
FIG. 2B is a view of the proximal end of the insert of FIG. 1A.
Figure 2C:
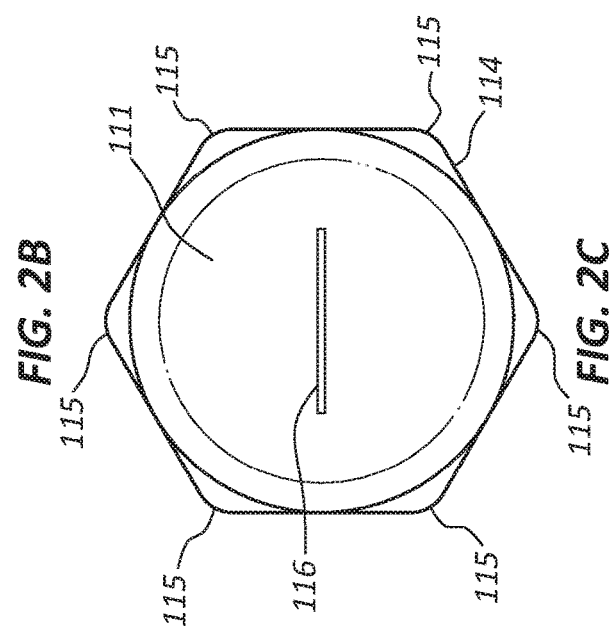
FIG. 2C is a view of the distal end of the insert of FIG. 1A.

In FIGS. 2A-2C, a cross section view, a bottom view, and a top view of the insert 110 are shown. The insert 110 is configured to be retained within the female cap 150 and to dispense disinfecting solution when the disinfecting cap 100 is coupled to a medical valve connector. The insert 110 comprises a top surface 111, a cavity or reservoir 113, a first circumferential groove 125, a second circumferential groove 126, a circumferential rib 112, and a retention feature 114. The insert 110 may be formed from any suitable polymeric and/or elastomeric material, such as silicone rubber, thermoplastic elastomer, rubber, other silicones, isoprene, neoprene, Santoprene, etc. The insert 110 may be manufactured using any suitable manufacturing technique, such as injection molding, compression molding, transfer molding, casting, liquid silicone rubber molding, etc. The insert 110 is cylindrical in shape with a closed distal end and an open proximal end with the cavity 113 disposed between the ends.

In some embodiments, the top surface 111 is disposed at the distal end of the insert 110. The top surface 111 is configured to be flat and perpendicular to the longitudinal axis of the insert 110. The flat configuration of the top surface 111 is configured to couple with the medical valve connector without actuating the valve of the medical valve connector. In other words, the geometry of the top surface 111 may be configured to minimize the probability the insert 110 will actuate or open the valve when coupling the cap 100 to the medical valve connector. For example, the top surface 111 may have a diameter larger than the diameter of the valve of the medical valve connector and therefore will not actuate the valve of the medical valve connector during or after coupling with the cap 100. Actuation of the valve of the medical valve connector may allow the disinfecting solution to enter the medical valve connector and the blood stream of the patient resulting in harm to the patient, especially neonate patients. Thus, the flat top surface 111 is configured to reduce the risk of harm to the patient.

In other embodiments, at least one aperture or slit 116 may be disposed in the top surface 111. The slit 116 may extend through the full thickness of the top surface 111. The slit 116 may be disposed in any suitable location. The slit 116 may comprise a single slit or a double slit where the slits cross and are perpendicular to one another. Any suitable number and orientation of slits 116 are contemplated. The slit 116 may be configured to facilitate loading of the disinfecting cap 100 with disinfecting solution. For example, during manufacturing of the assembly, a needle may penetrate the top surface 111 through the slit 116 to load disinfecting solution into the cavity 113. Upon removal of the needle, the slit 116 closes to seal disinfecting solution in the cavity 113. Disinfecting solution is intended to disinfect the medical valve connector of up to 100% of bacteria, viruses, and fungi. The disinfecting solution may be any suitable medical grade disinfecting solution, such as phenolics, quats, sodium hypochorite, chlorine dioxide, hydrogen peroxide, peracetic acid, glutaraldehyde, formaldehyde, alcohols, including isopropyl alcohol, etc.

In some embodiments, the insert 110 may comprise a second aperture or slit 117 disposed in a lateral wall of the insert 110. In some embodiments, the second slit may be configured as a perforation or a passage through the lateral wall of the insert. The second slit 117 may be disposed adjacent the top surface 111 and be oriented parallel to the longitudinal axis of the insert 110. The second slit 117 may be configured to open when the insert 110 is longitudinally compressed such that disinfecting solution is dispensed from the cavity 113 into the female cap 150 to disinfect the end of the medical valve connector with disinfecting solution. In some embodiments, the insert 110 may not comprise the second slit 117.

Referring to FIG. 2A, the insert 110 is shown to have a first groove 125 disposed adjacent the top surface 111, a second groove 126 disposed adjacent the proximal end of the insert 110, and a rib 112 disposed between the first groove 125 and the second groove 126. As shown in FIG. 4, the grooves 125, 126 are configured to collapse when the insert 110 is longitudinally compressed by the medical valve connector. The geometry of the insert may be configured such that one groove collapses before the other. For instance, in the illustrated embodiment, the second groove 126 is configured to collapse prior to the collapse of the first groove 125. In the illustrated embodiment, the width $D_1$ of the first groove 125 is less than the width $D_2$ of the second groove 126. The width $D_1$ may range from 30% to 70% of $D_2$, including 40% to 55%. A wall thickness $D_3$ of the insert 110 at the deepest point of the first groove 125 is configured to be greater than a wall thickness $D_4$ at the deepest point of the second groove 126. The wall thickness $D_4$ may range from 50% to 90% of $D_3$, including 70% to 85%. The combination of the thinner wall thickness $D_4$ and the wider width $D_2$ of the second groove 126 facilitates collapsing of the second groove 126 prior to the collapsing of the first groove 125 when the insert 110 is longitudinally compressed 110. In some embodiments, the grooves 125, 126 and rib 112 may be disposed on an interior surface of the insert 110.

The retention feature 114 is configured to couple the insert 111 to the female cap 150. The retention feature 114 may be disposed adjacent the proximal end of the insert 110 or at any suitable location along the longitudinal axis of the insert 110. The retention feature 114 is configured to have portions with a maximum diameter greater than a diameter of the top surface 111 and portions with a minimum diameter approximately equal to the diameter of the top surface 111. The shape of the retention feature 114 may be configured as any suitable polygon, such as a triangle, a square, a pentagon, a hexagon, etc. Laterally extending points 115 of the retention feature 114 are configured to interface with internal threads 153 of FIG. 3B such that the insert 110 is retained within the female cap 150. The portions of the retention feature 114 between the points 115 are configured to allow for flow of the disinfecting solution around the retention feature 114 when pressure is increased in the cavity 113 as the insert 110 is longitudinally compressed and collapsed.

Figure 3B:
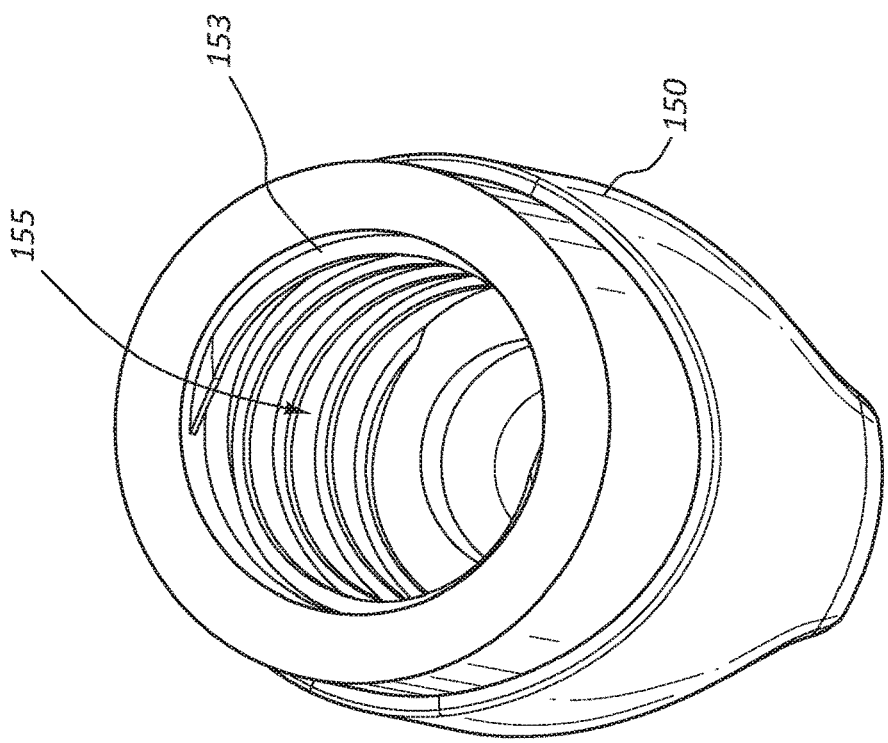
FIG. 3B is a perspective view of the female cap of the disinfecting cap of FIG. 1A.
Figure 3A:
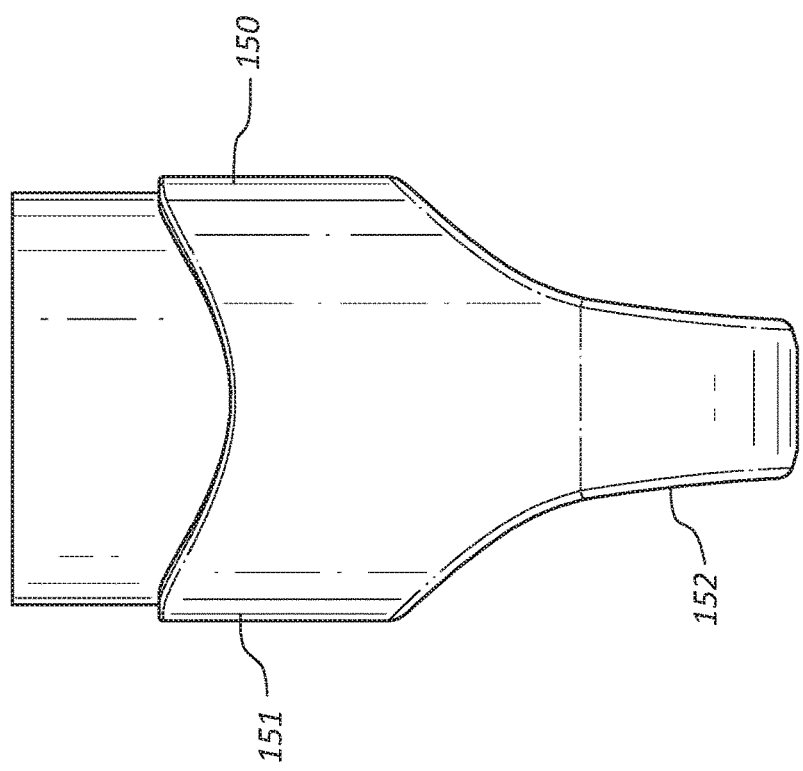
FIG. 3A is a side view of a female cap of the disinfecting cap of FIG. 1A.

Referring to FIGS. 3A-3B, the female cap 150 of the disinfecting cap 100 is shown. The female cap 150 comprises a body 151 and a bore 155. The body 151 may comprise finger grips 152 disposed at a proximal end portion of the body 151. The finger grips 152 are configured for grasping and twisting of the disinfecting cap 100 by fingers of the healthcare worker. A surface of the finger grips 152 may be modified to enhance the gripability of the female cap 150. Any suitable technique may be used to modify the finger grips, such as surface roughening, texturing, dimpling, recessing, overmolding, etc. The bore 155 is disposed within the body 151. The proximal end of the bore 155 is closed and may extend into the proximal end portion of the body 151. The distal end of the bore 155 is open at the distal end of the body 151. Internal threads 153 are disposed on an internal surface of the bore 155. The internal threads 153 are configured to engage with external threads of the medical valve connector. The female cap 150 may be formed from any suitable rigid or semi-rigid polymer, such as polypropylene, polyethylene, polycarbonate, etc. The female cap 150 may be manufactured using any suitable technique, such as injection molding, machining, casting, etc.

Figure 4A:
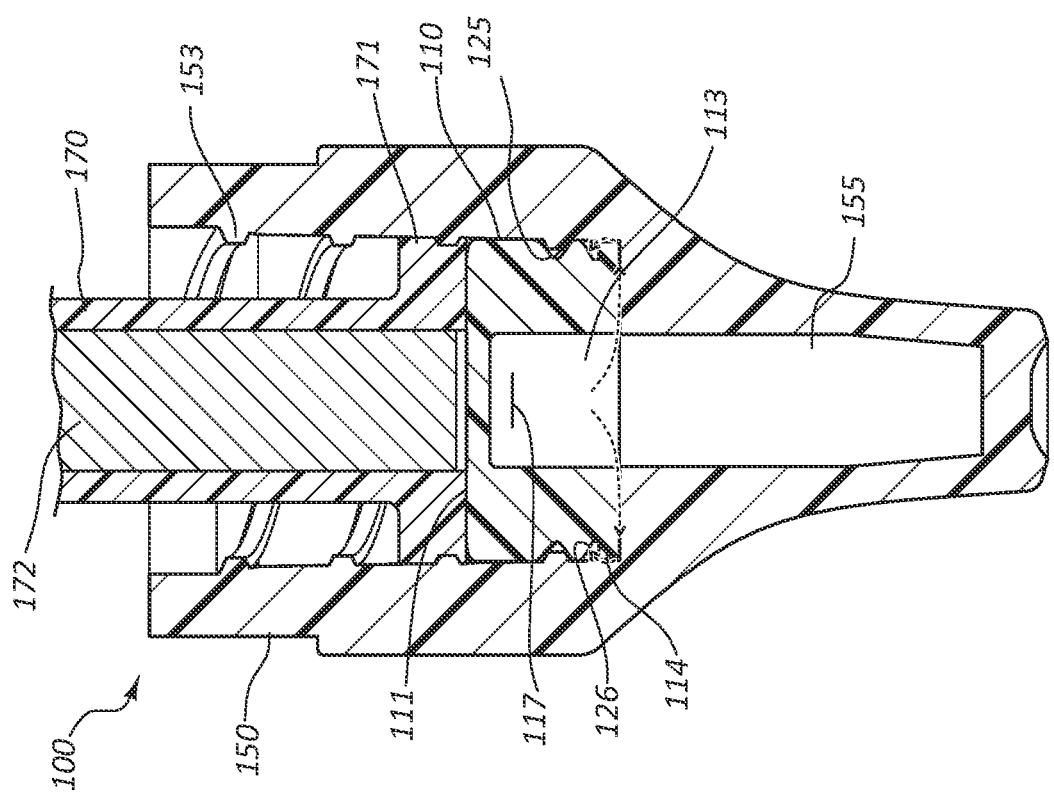
FIG. 4A is a cross section view of the disinfecting cap of FIG. 1A and a medical valve connector partially coupled to the disinfecting cap.
Figure 4B:
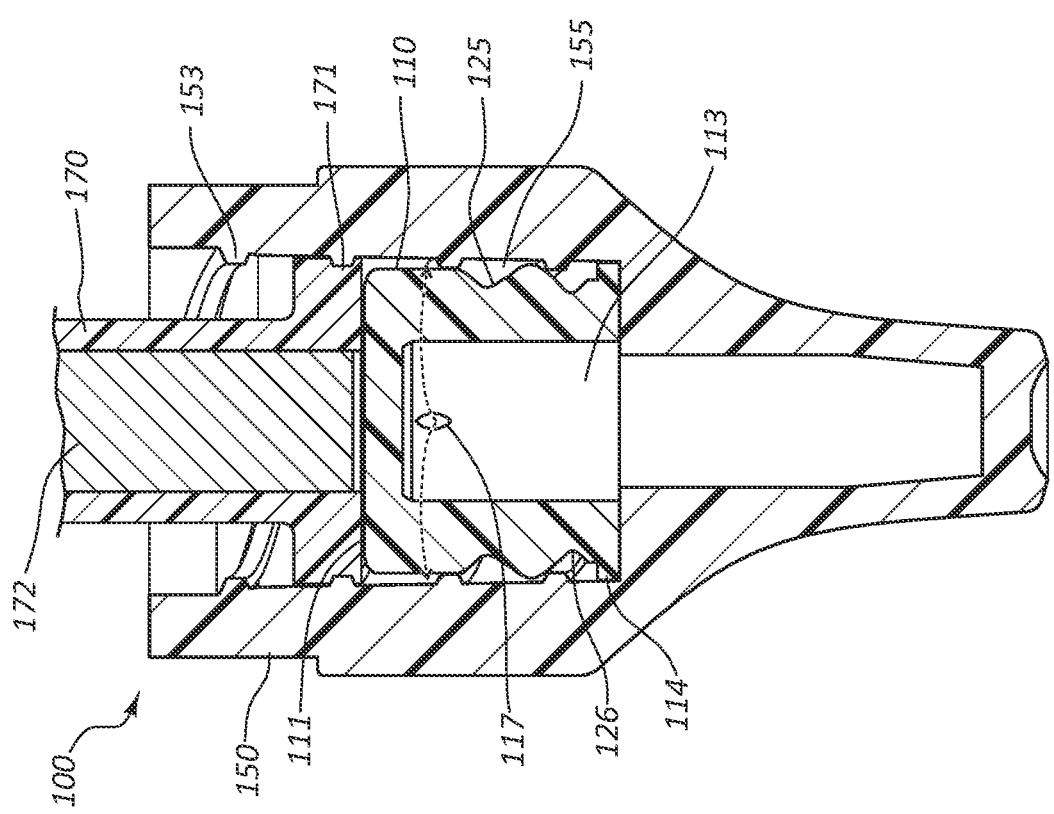
FIG. 4B is a cross section view of the disinfecting cap of FIG. 1A and a medical valve connector fully coupled to the disinfecting cap.

Referring now to FIGS. 4A-4B, the disinfecting cap 100 is shown coupled to a medical valve connector 170. As illustrated FIG. 4A, a proximal end portion of the medical valve connector 170 is partially disposed within the bore 155 of the female cap 150. External threads 171 of the medical valve connector 170 are coupled with the internal threads 153 of the bore 155 as the disinfecting cap 100 is twisted onto the medical valve connector 170. The points 115 of the retention feature 114 are disposed proximal to the internal threads 153 such that the insert 110 is retained within the bore 155. The insert 110 is partially compressed such that the second groove 126 of the insert 110 is collapsed. The second slit 117 is opened by the compression, allowing the disinfecting solution contained in the cavity 113 to flow into the bore 155 (as shown by the arrows).

In the relative configuration of FIG. 4B, the proximal end portion of medical valve connector 170 is fully disposed within the bore 155. The external threads 171 of the medical valve connector 170 are coupled to the internal threads 153 of the bore 155. The insert 110 is fully compressed such that both the first groove 125 and the second groove 126 are collapsed. The second slit 117 is compressed closed such that disinfecting solution cannot flow through the second slit 117. In some instances, when the assembly is in this state, the pressure within the cavity 113 may be high enough to force the flow of the disinfecting solution from the opening of the cavity 113, between the points 115 of the retention feature 114, and into the bore 155 (as shown by the arrows). The top surface 111 is coupled with the distal end of the medical valve connector 170 such that a valve 172 of the medical valve connector 170 is not actuated. That is, the top surface 111 of the insert 110 is configured to not apply an axial force to the valve 172 of the medical valve connector 170.

In some embodiments, disinfectant may only be released through the second slit 117 and not through the opening of the cavity 113. The amount of disinfectant released through the second slit 117 and the amount (if any) released through the opening of the cavity 113 may be tuned or controlled by the amount of disinfectant loaded into the cavity 113, the relative size of the cavity 113, the geometry of the insert 111, and so forth. Embodiments wherein the majority of (or all of) the disinfectant is released via the second slit 117 and embodiments wherein the majority of (or all of) the disinfectant is released via the opening of the cavity 113 are within the scope of this disclosure. Other release openings or points are also within the scope of this disclosure.

Figure 5B:
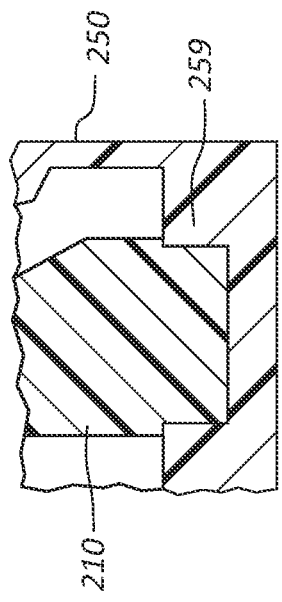
FIG. 5B is a cross section view of a retention feature of the disinfecting cap of FIG. 5A.
Figure 5C:
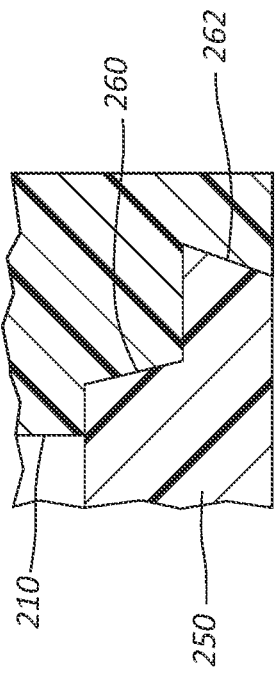
FIG. 5C is a cross section view of another embodiment of the retention feature of FIG. 5A.
Figure 5D:
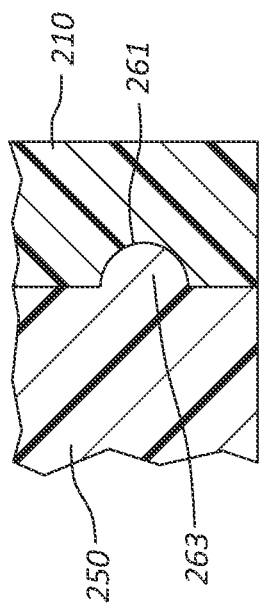
FIG. 5D is a cross section view of another embodiment of the retention feature of FIG. 5A.
Figure 5A:
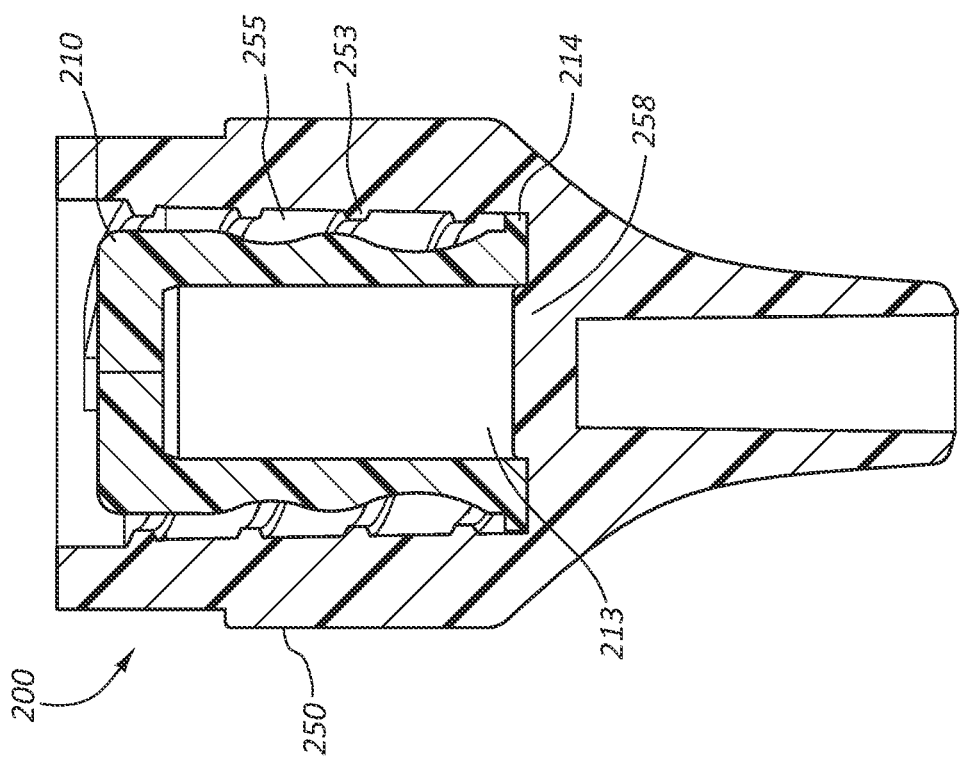
FIG. 5A is a cross section view of an embodiment of the disinfecting cap having a protrusion to retain an insert.

Referring now to FIGS. 5A-5D, another embodiment of a disinfecting cap 200 is illustrated. FIGS. 5A-5D illustrate a disinfecting cap 200 comprising a female cap 250, an insert 210, and embodiments of features configured to retain the insert 210 within the female cap 250. FIG. 5A illustrates a retention feature 214 similar to the retention feature 114 discussed previously and a protrusion 258. The protrusion 258 is configured to extend distally from an end wall of a bore 255. The protrusion 258 is configured to extend into a cavity 213 of the insert 210 with an interference fit such that the insert 210 is retained by the protrusion 258. Additionally, the interference fit is configured to seal the cavity 213 such that disinfecting solution discussed above is retained in the cavity 213 until a fluid force exceeding a sealing force is exceeded when the insert 210 is axially compressed by the medical valve connector 170.

FIG. 5B illustrates a portion of the insert 210 and the female cap 250. The insert 210 may or may not comprise the retention feature 214. The female cap 250 is shown to comprise an annular recess 259 into which a portion of the insert 210 is disposed with an interference fit. The coupling of the insert 210 with the annular recess 259 is configured to retain the insert 210 within the female cap 250 and seal the disinfecting solution within the cavity 213. Disinfecting solution may flow through the annular recess 259 when pressure within the cavity 213 is increased as the insert 210 is compressed by the medical valve connector.

FIG. 5C illustrates a portion of the insert 210 and the female cap 250. The insert 210 comprises a multi-angled and stepped retention feature 260. The retention feature 260 is configured to sealingly couple to a matching recess 262 in the female cap 250, such that the insert 210 is retained within the female cap 250 and disinfecting solution is sealed within the cavity 213. Disinfecting solution may flow past the retention feature 260 and the recess 262 when pressure within the cavity 213 is increased as the insert 210 is compressed by the medical valve connector.

FIG. 5D illustrates a portion of the insert 210 and the female cap 250. The insert comprises a semicircular annular recess 261 extending around the circumference of the insert 210. The recess 261 is configured to sealingly couple with a matching annular rib 263 of the female cap 250, such that the insert 210 is retained within a bore 255 and the disinfecting solution is sealed within the cavity 213. Disinfecting solution may flow by the recess 261 and the rib 263 when pressure within the cavity 213 is increased as the insert 210 is compressed by the medical valve connector.

Figure 6B:
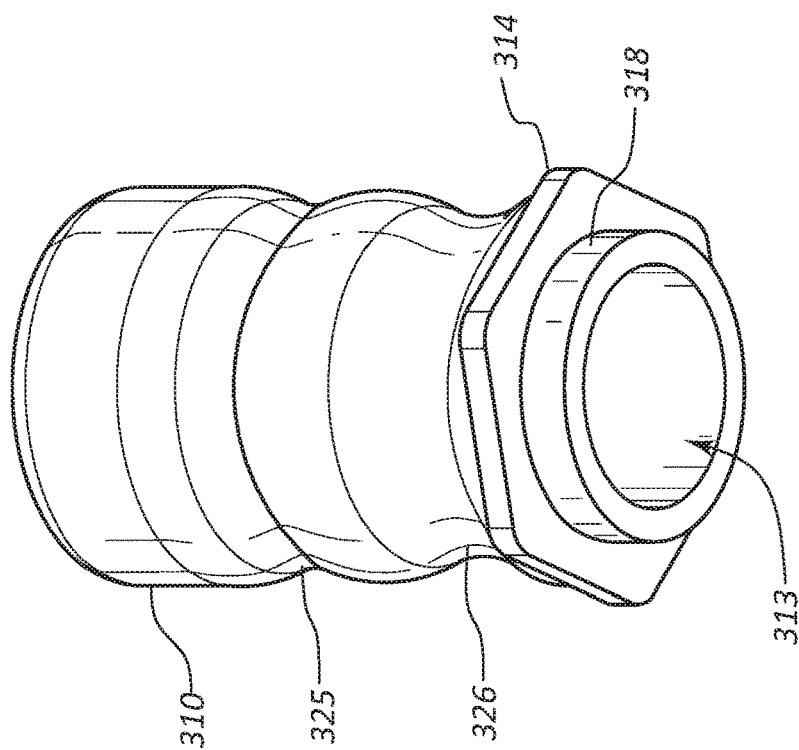
FIG. 6B is a perspective view of the insert of the disinfecting cap of FIG. 6A.
Figure 6A:
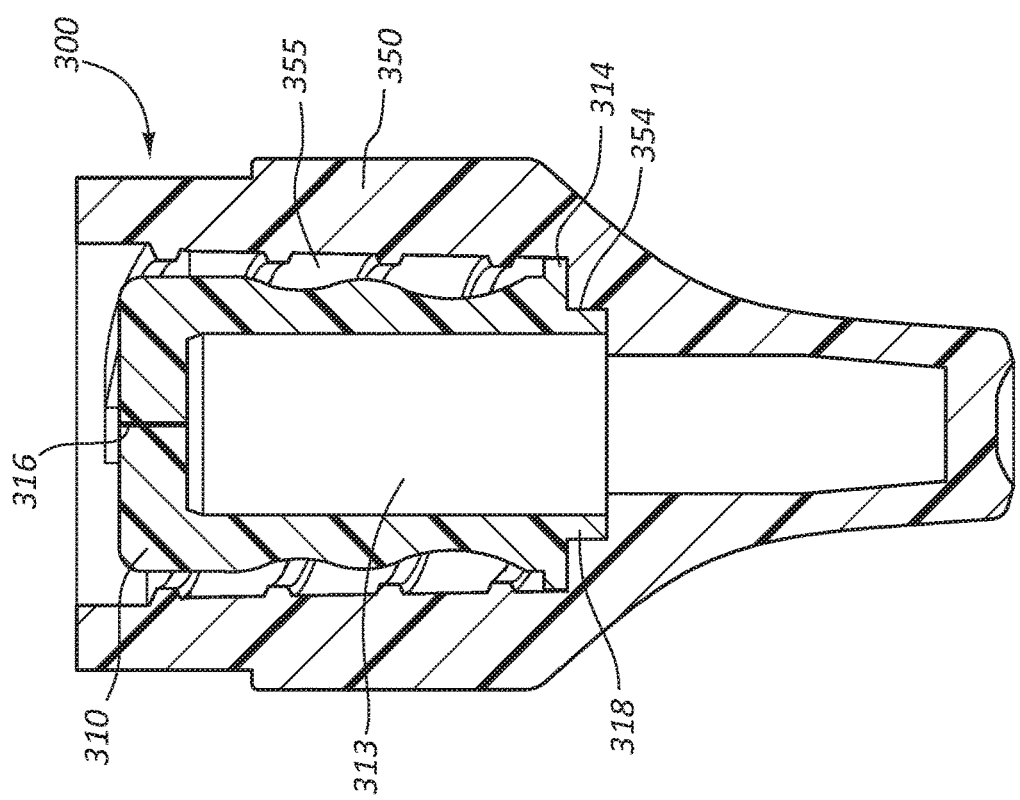
FIG. 6A is a cross section view of an embodiment of the disinfecting cap having a retention ring.

Referring to FIGS. 6A and 6B, another embodiment of a disinfecting cap 300 is shown. The disinfecting cap 300 comprises a female cap 350 and an insert 310. The insert 310 may or may not comprise a retention feature 314 similar to the retention feature 114 described previously. A retention ring 318 extends proximally from an open end of the insert 310. The retention ring 318 is configured to sealingly couple with a portion of a bore 355 of the female cap 350, such that the insert 310 is retained within the bore 355 and disinfecting solution is sealed within the cavity 313.

Referring to FIGS. 7A-7D, yet another embodiment of the disinfecting cap 400 is illustrated. The disinfecting cap 400 comprises a female cap 450 and an insert 410. The insert comprises a retention feature 414 and a seal member 419. The seal member 419 is coupled to the proximal end of the insert 410, such that a cavity 413 containing the disinfecting solution is sealed at a proximal end. In some embodiments, the seal member 419 may be coupled to a proximal portion of a lateral wall of the seal member 419. The seal member 419 may comprise a laminated film comprising a foil layer 421 laminated between polymer layers 420 as shown in FIG. 7C. The foil layer 421 may comprise any suitable malleable foil material, such as aluminum, copper, tin, etc. The foil layer 421 may comprise a perforation 422, as shown in FIG. 4B. The perforation 422 may be configured to tear open and remain open to allow the disinfecting solution to flow from the cavity 413, around the retention feature 414, and into the bore 455. The perforation 422 may tear open when pressure within the cavity 413 exceeds the strength of the perforation 422. The pressure in the cavity 413 increases when the insert 410 is axially compressed by the medical valve connector. The polymer layers 420 may comprise any suitable polymer, such as polyethylene, polypropylene, etc. The seal member 419 may be sealingly coupled to the insert 410 utilizing any suitable manufacturing technique, such as heat bonding, welding, ultrasonic welding, adhesives, overmolding, insert molding, etc.

Figure 8:
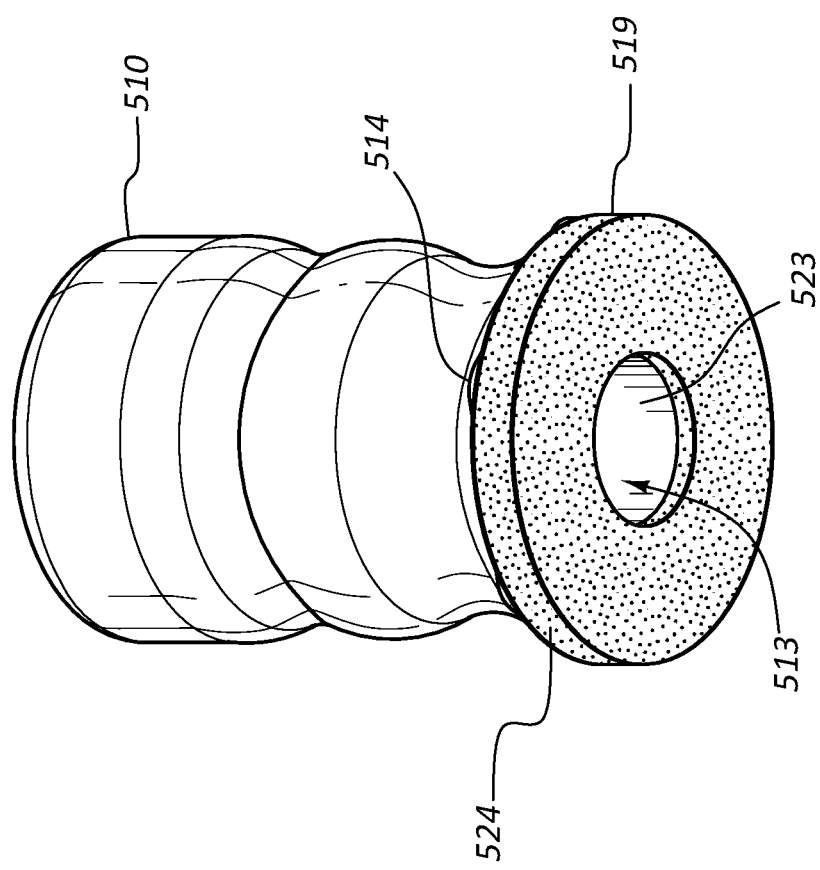
FIG. 8 is a perspective view of an insert having a laminate seal.

Referring now to FIG. 8, another embodiment of a seal member 519 is shown. The seal member 519 comprises a similar laminated structure and materials as the seal member 419 and is coupled to an insert 510 using similar manufacturing techniques as described above. The seal member 519 comprises a passage 523 configured to provide fluid communication between a cavity 513 of the insert 510 and a bore of a female cap. A peripheral portion 524 of the seal member 519 may be folded to surround a retention feature 514 of the insert 510, such that a seal between the seal member 519 and the bore of the female cap is formed.

FIGS. 9A and 9B illustrate yet another embodiment of a disinfecting cap 600. The disinfecting cap 600 comprises a female cap 650 and an insert 610. The female cap 650 comprises a bore 655 and a retention ring 654 extending radially inward from a wall of the bore 655. The retention ring 654 may be disposed proximally of internal threads 653. The insert 610 comprises a cavity 613 configured to be in fluid communication with the bore 655. The insert 610 further comprises a retention feature 614 extending radially outward from an exterior surface of the insert 610. The retention feature 614 may be disposed distally of a first groove 625. The retention feature 614 is configured to sealingly couple with the retention ring 654, such that the insert 610 is retained within the bore 655. Disinfecting solution is sealed within the bore 655 and the cavity 613 until the retention feature 614 is displaced from engagement with the retention ring 654. A proximal end of the insert 610 may be disposed upon a shoulder 657 within the bore 655.

Figure 10B:
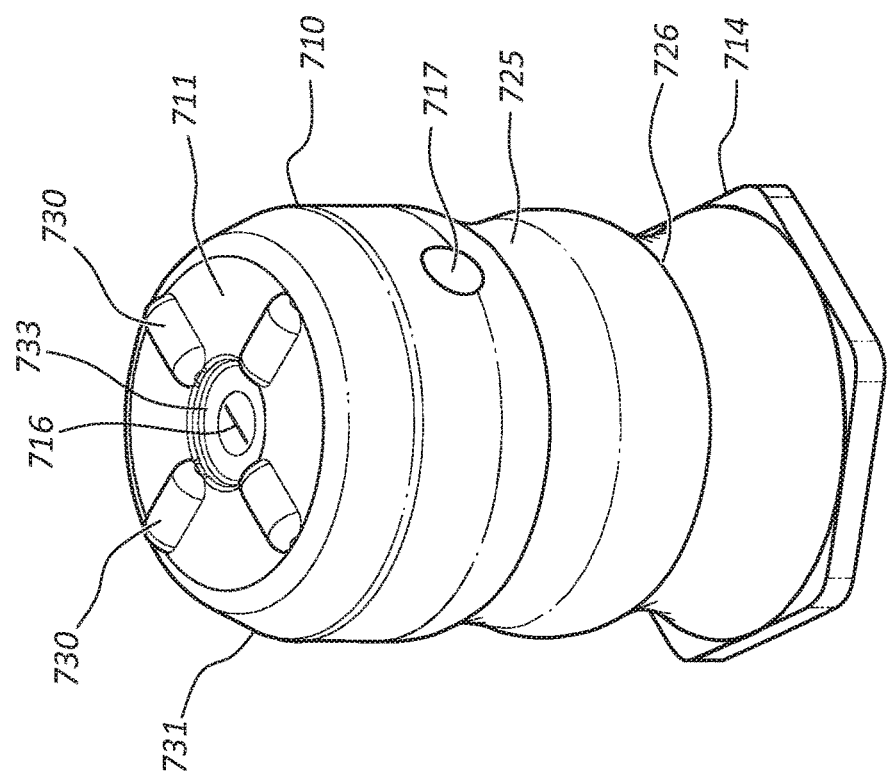
FIG. 10B is a perspective view of the insert of the disinfecting cap of FIG. 10A.
Figure 10A:
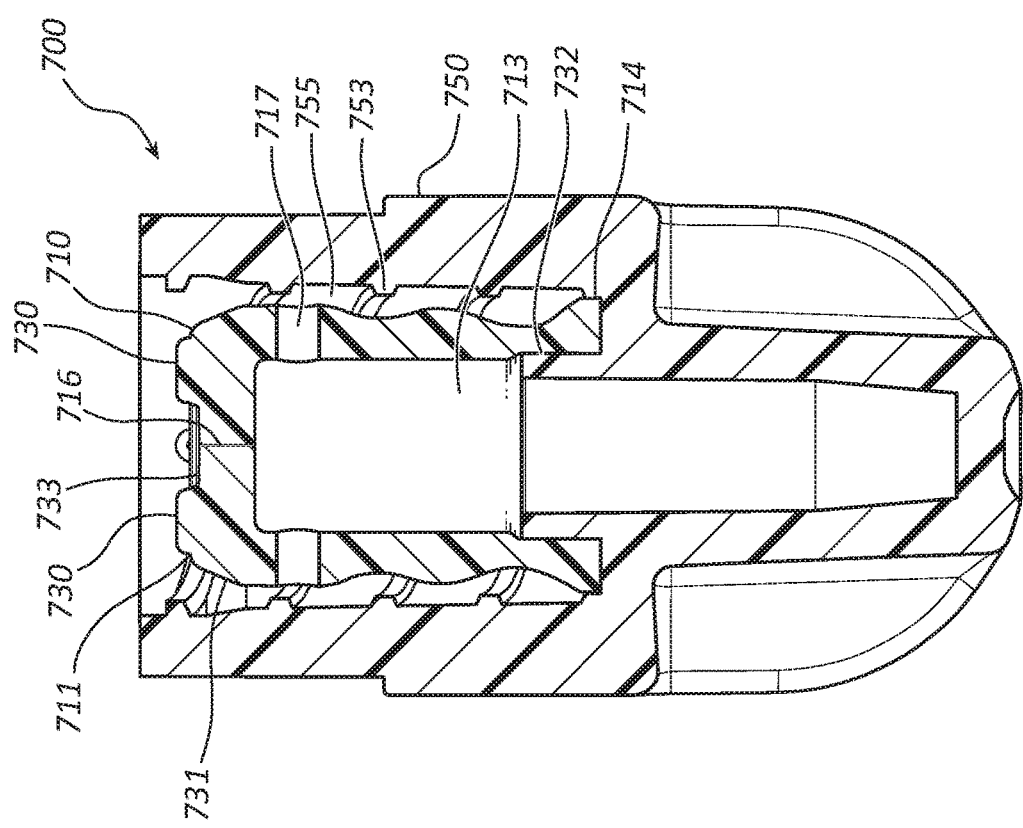
FIG. 10A is a cross section view of an embodiment of the disinfecting cap having top surface protrusions or wipers.

Referring to FIGS. 10A and 10B, another embodiment of a disinfecting cap 700 is shown. The disinfecting cap 700 comprises a female cap 750 and an insert 710. The insert 710 may comprise a retention feature 714 similar to the retention feature 114 described previously. As shown in FIG. 10A, the female cap 750 has an internal cylindrical riser 732 that may be frictionally coupled to a surface of a cavity 713 of the insert 710. The height of the riser 732 may range from about 0.025 inch to about 0.100 inch. The riser 732 may displace the retention feature 714 radially outward such that the retention feature 714 engages with a wall of a bore 755 of the female cap 750. The retention feature may be displaced from about 0.005 inch to about 0.015 inch due to interaction with the riser 732. Stated another way, the outer diameter of the riser 732 is about 0.005 inch to about 0.015 inch larger than the inner diameter of the cavity 713.

As illustrated in FIGS. 10A and 10B, the insert 710 includes a first groove 725 and a second groove 726 configured to sequentially collapse when the insert 710 is longitudinally compressed as previously described. The insert 710 also includes one or more apertures or openings 717 disposed in a lateral wall of the insert 710. The opening 717 may be configured to allow disinfecting solution to pass from the cavity 713 into the bore 755 when the insert 710 is longitudinally compressed. In certain embodiments, the opening 717 may close when the insert 710 is longitudinally compressed to prevent flow of disinfecting solution. In other embodiments, the opening 717 remains open when in an uncompressed state and may equalize atmospheric pressure within the cavity 713 and the bore 755 such that the insert 710 is not dislodged from the riser 732 with changes of atmospheric pressure. A second aperture or slit 716 is shown to be disposed in a top surface 711 of the insert 710. The second slit 716 may be configured for passage of a cannula during manufacturing of the disinfecting cap 700 to fill the cavity 713 with disinfecting solution.

The top surface 711 includes a plurality of protrusions or wipers 730 extending upwardly. The number of protrusions 730 may be 2, 3, 4, 5, 6, 7, 8, or more. Each protrusion 730 may be elongate and extend radially outward from a central recess 733. The protrusions 730 may be equally spaced around the top surface 730. For example, as illustrated in FIG. 10B, the protrusions 730 are spaced 90 degrees apart around the disk shaped top surface 711. The protrusion 730 may be radiused from side to side and may have a height of between about 0.005 in and about 0.025 inch. In other embodiments, the protrusion 730 may be defined as a discontinuous ring, a single protrusion extending across the top surface 711, a scalloped protrusion, and so forth. The protrusion 730 may be configured to wipe and clean a proximal surface of a medical valve connector as the medical valve connector is rotatably decoupled from the disinfecting cap 700. Additionally, the protrusion may be configured to form a gap between the top surface 711 and the proximal surface of the medical valve connector to allow disinfecting solution to flow over the top surface 711 and over the proximal end of the medical valve connector when the medical valve connector is coupled to the disinfecting cap. The protrusion 730 may be an integral part of the top surface 711 and formed from the same elastomeric material as the top surface 711. In certain embodiments, the protrusion 730 may be a separate element formed from a rigid or semi-rigid thermoplastic material and coupled to the top surface 711. In one exemplary embodiment, the protrusion 730 may be more rigid than the top surface 711.

The top surface 711 may also comprise a chamfer 731 extending radially outward from the top surface 711 to the lateral wall of the insert 710. The chamfer 731 may be configured to reduce a diameter of the top surface 711 such that an outer edge of the top surface 711 is not pinched or torn in the internal threads 753 when the disinfecting cap 700 is rotatably coupled to the medical valve connector In use, a medical valve connector may be coupled to an infusion therapy delivery system configured to deliver therapeutic fluids to a patient. Upon completion of an infusion therapy treatment, the infusion therapy delivery system is decoupled from the medical valve connector. Any one of the disinfecting cap embodiments described above may be coupled to the medical valve connector to disinfect the medical valve connector and prevent an infection of a patient.

An open end of the disinfecting cap is disposed over the proximal end of the medical valve connector such that external threads of the medical valve connector and internal threads of the disinfecting cap engage. The disinfecting cap is twisted such that the disinfecting cap is drawn over the medical valve connector. The medical valve connector couples to an insert disposed within the disinfecting cap. The insert comprises a top surface configured to be flat such that the top surface does not actuate a valve of the medical valve connector when the insert and the valve are coupled. As the disinfecting cap is drawn over the medical valve connector, the insert is axially compressed, resulting in dispensing of disinfecting solution contained within a cavity of the insert. Disinfection solution is dispensed through a slit disposed in a lateral wall of the insert and/or around a retention feature configured to retain the insert within the disinfecting cap. The dispensed disinfecting solution interacts with and disinfects the proximal end of the medical valve connector. The insert is configured to be axially compressed as at least two annular grooves collapse. The grooves are configured such that a first groove will collapse prior to a second groove as the insert is compressed.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "about." For each such reference, it is to be understood that, in some embodiments, the value, feature, or characteristic may be specified without approximation. For example, where a qualifier such as "about" is used, this term includes within its scope the qualified word in the absence of its qualifier. For example, where the term "about 0.005 inch" is recited with respect to a feature, it is understood that in further embodiments the feature can be precisely 0.005 inches.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art may use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A disinfecting medical device, comprising:
    a cap comprising a bore; and
    an insert disposed within the bore;
    wherein the insert comprises an open first end and a selectively closed second end;
    wherein the insert is configured to longitudinally collapse and dispense a disinfecting solution from an insert cavity;
    wherein the insert cavity extends from the open first end to the selectively closed second end;
    wherein the insert further comprises:
        a top surface;
        a first aperture disposed in the top surface;
        a second aperture disposed in a lateral wall;
        a first circumferential groove;
        a circumferential rib disposed between the first groove and the second groove;
        a retention feature; and
    wherein the insert is configured to longitudinally collapse at the second groove prior to longitudinally collapsing at the first groove.

2. The disinfecting medical device of claim 1, wherein the device is configured to couple with a medical valve connector and disinfect a portion of the medical valve connector.

3. The disinfecting medical device of claim 1, wherein the device is configured to couple with a medical valve connector such that a valve of the medical valve connector is not actuated.

4. The disinfecting medical device of claim 1, wherein a width of the first groove is less than a width of the second groove.

5. The disinfecting medical device of claim 1, wherein the retention feature is configured to retain the insert within the bore and to permit flow of the disinfecting solution from the cavity into the bore.

6. The disinfecting medical device of claim 1, wherein the insert is sealingly coupled to the cap.

7. The disinfecting medical device of claim 1, wherein the first aperture is configured for filling the cavity with the disinfecting solution and the second aperture is configured to dispense the disinfecting solution into the bore when the insert is longitudinally compressed.

8. The disinfecting medical device of claim 1, wherein the second aperture is a slit configured to open when the insert is longitudinally compressed.

9. The disinfecting medical device of claim 1, wherein the second aperture is an opening configured to close when the insert is longitudinally compressed.

10. The disinfecting medical device of claim 1, wherein the top surface comprises a plurality of protrusions configured to wipe a proximal surface of a medical valve connector when the medical valve connector is rotatably decoupled from the disinfecting medical device.

11. The disinfecting medical device of claim 10, wherein the plurality of protrusions are configured to allow disinfecting solution to flow over the top surface when the disinfecting medical device is coupled to the medical valve connector.

12. A medical system configured to cover and disinfect a medical valve connector, comprising:
    a cap comprising a bore, wherein the bore comprises internal threads; and an insert disposed within the bore, wherein the insert comprises:
        an open first end and a selectively closed second end;
        a top surface disposed at the selectively closed second end;
        a first circumferential groove;
        a second circumferential groove;
        a circumferential rib disposed between the first groove and the second groove;
        a cavity extending from the open first end to the selectively closed second end; and
        a retention feature;
        wherein the insert is configured to longitudinally collapse and dispense a disinfecting solution from the cavity; and
        wherein a width of the first groove is less than a width of the second groove, wherein the second groove collapses prior to the first groove when the insert is longitudinally compressed.

13. The medical system of claim 12, wherein the retention feature is configured to couple with the internal threads, such that the insert is retained within the bore.

14. The medical system of claim 12, wherein the insert further comprises a first aperture disposed in the top surface and a second aperture disposed in a lateral wall.

15. The medical system of claim 12, wherein the top surface comprises a plurality of protrusions configured to wipe a proximal surface of a medical valve connector when the medical valve connector is rotatably decoupled from the cap.

16. The medical system of claim 15, wherein the plurality of protrusions are configured to allow the disinfecting solution to flow over the top surface when the cap is coupled to the medical valve connector.

17. A method of disinfecting a medical valve connector, comprising:
    obtaining a disinfecting cap, wherein the disinfecting cap comprises:
        a bore; and
        an insert disposed within the bore;
        wherein the insert comprises an open first end and a selectively closed second end;
        wherein the insert is configured to longitudinally collapse and dispense a disinfecting solution from an insert cavity;
        wherein the insert cavity extends from the open first end to the selectively closed second end;
        wherein the insert further comprises:
            a top surface;
            a first aperture disposed in the top surface;
            a second aperture disposed in a lateral wall;
            a first circumferential groove;
            a circumferential rib disposed between the first groove and the second groove;
            a retention feature; and
        wherein the insert is configured to longitudinally collapse at the second groove prior to longitudinally collapsing at the first groove;
    coupling the disinfecting cap to the medical valve connector, wherein the insert is compressed longitudinally and the disinfecting solution is dispensed from the cavity of the insert; and
    bathing an end of the medical valve connector in the disinfecting solution.

18. The method of claim 17, further comprising:
    rotatably decoupling the disinfecting cap from the medical valve connector; and wiping the end of the medical valve connector with a plurality of protrusions disposed on a top surface of the insert.

* * * * *